United States Patent [19]

Patterson

[11] Patent Number: 4,969,876
[45] Date of Patent: Nov. 13, 1990

[54] NEEDLE PROTECTOR

[75] Inventor: W. Michael Patterson, Richmond, Ind.

[73] Assignees: Frank LaVallo; Raymond F. Ontko, both of Richmond, Va.; part interest to each

[21] Appl. No.: 404,261

[22] Filed: Sep. 7, 1989

[51] Int. Cl.5 .............................................. A61M 5/00
[52] U.S. Cl. ................................... 604/171; 604/177; 604/198; 604/110
[58] Field of Search ............... 604/110, 171, 174, 177, 604/180, 162, 164, 165, 198, 263

[56] References Cited

U.S. PATENT DOCUMENTS

| 3,064,648 | 11/1962 | Bujan. | |
|---|---|---|---|
| 3,856,020 | 12/1974 | Kovac. | |
| 3,973,565 | 8/1976 | Steer. | |
| 4,161,177 | 7/1979 | Fuchs. | |
| 4,170,993 | 10/1979 | Alvarez. | |
| 4,349,022 | 9/1982 | Ishikawa. | |
| 4,366,817 | 1/1983 | Thomas. | |
| 4,627,842 | 12/1986 | Katz. | |
| 4,676,783 | 6/1987 | Jagger et al.. | |
| 4,772,264 | 9/1988 | Cragg. | |
| 4,781,692 | 11/1988 | Jagger et al. | 604/164 |
| 4,820,282 | 4/1989 | Hogan. | |
| 4,850,961 | 7/1989 | Wanderer et al. | 604/110 |
| 4,888,001 | 12/1989 | Schoenberg | 604/263 |

Primary Examiner—Stephen C. Pellegrino
Assistant Examiner—Ralph Lewis
Attorney, Agent, or Firm—Barnes & Thornburg

[57] ABSTRACT

A needle assembly of the so-called butterfly type in which the needle is retractable into its holder by pulling rearwardly on the flexible feed tube. The rearward movement of the needle is stopped by a turned portion of the holder which is turned after the needle is assembled into the holder.

9 Claims, 1 Drawing Sheet

NEEDLE PROTECTOR

BACKGROUND OF THE INVENTION

The present invention relates to needle assemblies of the type used with medical patients for infusion or extraction of fluids, particularly the provision of such an assembly arranged to prevent the very dangerous needle sticks after the needle has been used with a patient.

It is now well known in the medical field that one of the most dangerous activities is the handling of needles and syringes after they have been used with patients. Such used needles may well be contaminated with active and dangerous microbes, involved with diseases such as hepatitis and AIDS. One of the most dangerous needle assemblies used in treatment of patients is the so-called butterfly needle employed to introduce intravenous solutions in a drip or continuous flow. In the hospital environment, it is probably one of the most dangerous, in terms of medical and maintenance personnel getting stuck after a needle has been used. Immediately after withdrawal, the conventional butterfly needle swings about rather freely. Nurses and other technicians are very prone simply to drop the used butterfly needle in a wastebasket.

DESCRIPTION OF PRIOR ART

Since the problems with needle sticks are so well-known and currently being considered as a major problem to be solved in the medical industry, a wide variety of approaches have been offered to solve the problem. Many of these approaches involve providing some method for retracting the sharpened end of the needle into a container after the needle is used, i.e., after it is removed from the patient. U.S. Pat. No. 4,676,783 to Jagger, et al., for instance, discloses a butterfly intravenous needle which may be retracted into its carrier tube after it is used. The Jagger, et al., Patent discloses a hollow tube in which a needle and its connecting flexible tube are slidably movable. The rearward end of the tube is constricted at to capture an enlarged end of the flexible tube, thereby retaining the needle in the tube. While Jagger, et al., offers a retractable needle solution to the needle stick problem, the specific structure taught by Jagger, et al., would be very difficult to fabricate. In the disposable medical products business, the products must be extremely inexpensive, simple to manufacture and easy to use.

For examples of other prior art references showing extra accessories for covering a needle, see U.S. Pat. No. 4,820,282 to Hogan and U.S. Pat. No. 4,170,993 to Alvarez.

SUMMARY OF THE INVENTION

The present invention constitutes an improvement over known prior needle assemblies because it is extremely simple, efficient and inexpensive to manufacture, using a minimum number of parts and less material than prior art assemblies. The assembly of the present invention uses current assembly means and methods. The needle assembly of the present invention is used in the same manner as existing needle assemblies during insertion. The retraction of the needle itself into the assembly is easy to understand and use, and may be accomplished while the assembly is still taped to the patient.

It is an object of the present invention, therefore, to provide a needle assembly comprising a rigid, straight, hollow needle having a sharpened forward end and rearward end, flexible tube means connected to the rearward end of the needle, and an elongated outer tube slidably receiving the needle and at least a forward portion of the tube means. The outer tube has a straight length sufficient totally to receive the needle therein and a forward end formed to pass the forward sharpened end of the needle therethrough. The outer tube is also formed at its forward end to constrict the flexible tube means against forward movement. The outer tube has a rearward end portion turned at an angle, bent or curved relative to the longitudinal axis of the tube to prevent rearward movement of the needle, whereby, when the flexible tube means is pulled rearwardly from the outer tube, the needle is pulled rearwardly to a position totally within the outer tube to protect the sharpened end. The terms "turned at an angle", or "bent", or "curved" are intended to described an offset condition hereinafter. The needle is preferably pulled to a canted position within the outer tube when the flexible tube is pulled rearwardly, the canted position being obtained by pulling the needle rearward end into the outer tube rearward end portion which is turned. This turned rearward end portion provides a positive stop for the needle upon retraction relying upon a spring-loaded grasp rather than friction resistance to further movement.

Another object of the present invention is to provide such a needle assembly in which the outer tube is formed as an elongated cylindrical tube without internal restrictions for freely slidably receiving the needle and the at least forward portion of the tube means except for the forward end of the outer tube which is constricted to a size sufficient to pass the needle and to restrict the flexible tube means. This outer tube may preferably be molded from plastic with its rearward end portion turned at an angle sufficient to prevent rearward movement of the needle after the needle and the at least forward portion of the flexible tube means is inserted into the outer tube and moved forwardly. The outer tube may also preferably be molded with an integral breakaway needle cover that will, once it is broken away from the outer tube, discourage efforts to reuse it again as a cover. The needle sharpened end is always covered after assembly until the cover is removed, thereby preventing dulling of the needle. Further, the needle cover will not fall off inadvertently during packaging or in readying the assembly for use. Since the needle cover is preferably integrally molded with the outer tube, it will have the same coefficient of expansion.

Still another object of the present invention is to provide such an assembly in which the outer tube is molded to have diametrically opposed, radially outwardly and longitudinally extending wings which, when folded toward each other, provide a gripping means for the assembly and means for squeezing the outer tube to hold the needle against rearward movement therein when the wings are folded together. This squeezing means may preferably be disposed on the wings to squeeze the outer tube.

Thus, it is an overall object of this invention to provide an anti-needle stick intravenous needle assembly which reduces the risk of accidental needle stick injuries to health care professionals and other persons who use or participate in the disposal of intravenous needles.

It is also an object of this invention to provide such an intravenous needle assembly in which the means of protecting the needle after use remains with the needle at all times prior to, during, and after the use of the needle.

It is also an object of this invention to provide such a needle assembly which is economical to produce and easy to use.

It is also an object of this invention to provide such an intravenous needle assembly which is operated simply and with little additional manipulation to protect the needle point. In use of this invention, while the wings of the needle assembly are still taped to the patient, the needle may be pulled from the vein directly into the hollow outer tube to its needle protected position. The slightly turned or curved rearward portion of the outer tube will prevent removal of the needle from the rear end of the outer tube. Then, when the tape is removed to remove the assembly, the needle point is protected so that the assembly can be safely dropped into a waste container.

Other objects and features of the present invention will become apparent as this description progresses.

DETAILED DESCRIPTION OF THE DRAWINGS

Figure 1:
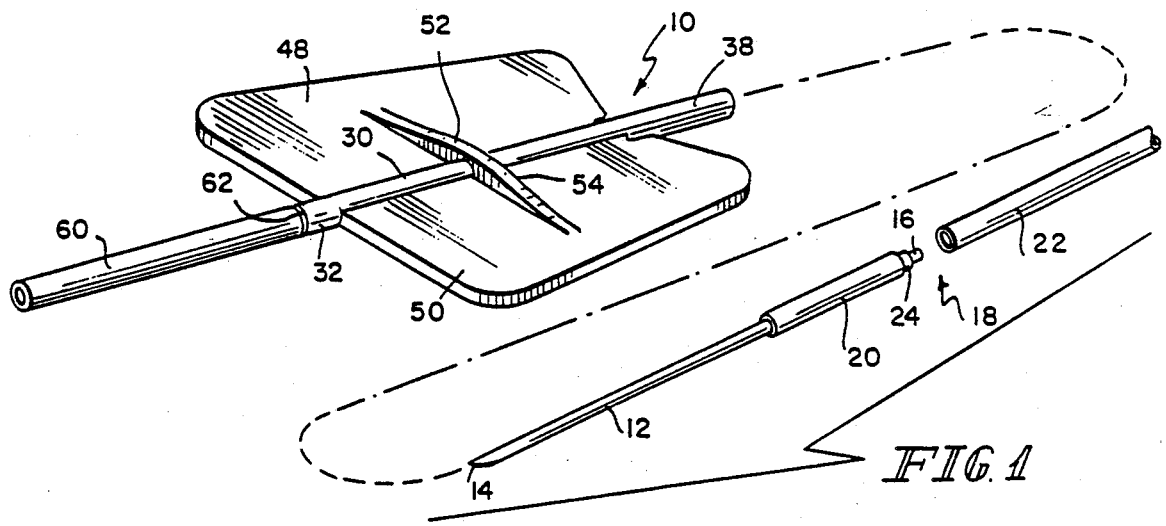
FIG. 1 is an exploded perspective view of the needle assembly of the present invention showing the bottom of the butterfly component.

Referring to the drawings, it will be seen that the needle assembly 10 comprises a conventional rigid, straight, hollow needle 12 having a sharpened forward end 14 and a rearward end 16 with flexible tube means 18 including a dowel-like plastic sleeve 20 formed on the rearward end portion of the needle to be connected to a flexible trailing tube 22. It will be seen that the flexible tube 22 is attached to the reduced rear portion 24 of the sleeve 20 and there bonded by conventional techniques.

Figure 2:
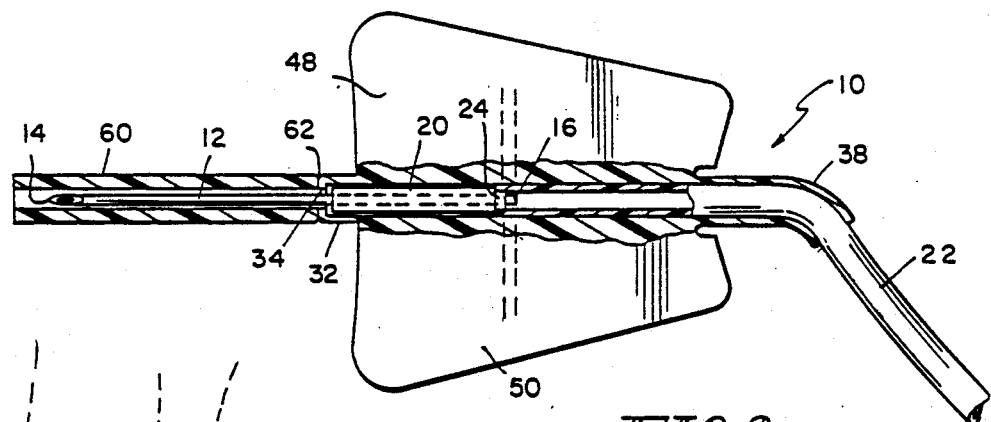
FIG. 2 is a fragmentary longitudinal sectional view of the assembly showing the top of the butterfly component.
Figure 3:
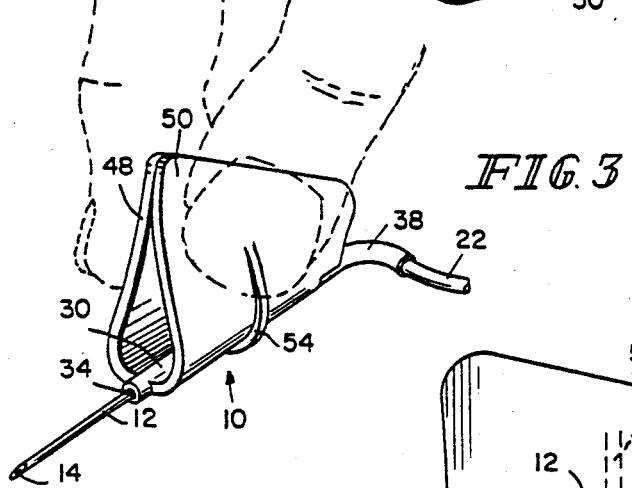
FIG. 3 is a perspective view showing the wings folded together to provide means for gripping the needle assembly.
Figure 4:
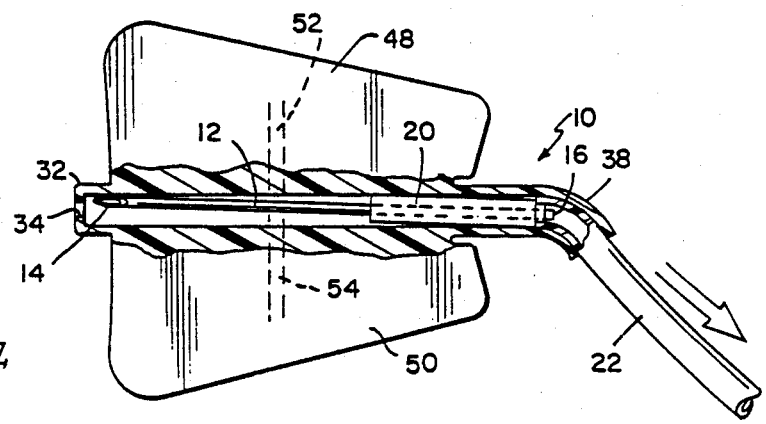
FIG. 4 is a fragmentary longitudinal sectional view showing the needle in its retracted position within the assembly.

The needle 12 and at least a forward end portion of the flexible tube means 18, principally the sleeve 20 and the forward end of the flexible tube 22, are inserted into an outer tube 30 having a forward end 32 constricted as indicated at 34 and a rearward end 38. Once the needle 12 and the forward portion of the tube means 18 is inserted into the tube 30 so that the needle 12 is passed through the forward end 32 of the tube 30 to be in its position clearly shown in FIG. 2, the rearward end portion 38 of the tube 30 may be formed as indicated in FIGS. 2, 3 and 4 to have a turned portion 38. This bending or turning of the rear end portion 38 and the flexible tube 22 disposed therein may be just sufficient to restrict the passage of the needle 12 rearwardly therethrough. The turning or bending of this rearward portion 38 may be accomplished by application of a slight amount of heat energy necessary to make the thermal plastic material from which the outer tube 30 is molded take a set. When the rearward end portion 38 is so turned as illustrated, the tube 30 is left with a straight portion of sufficient length to receive the entire needle 12 therein when the needle is retracted to its position shown in FIG. 4. In that position, the needle 12 is slightly canted relative to the tube 30 because of the turned portion 38 such that the sharpened end 14 is not likely to move again through the constricted opening 34.

The outer tube 30 preferably has an internal diameter sufficiently large and unrestricted to permit easy and loose insertion of the needle 12 and sleeve 20 therein.

In the preferred and illustrated embodiment, the tube 30 is molded with diametrically opposed, radially outwardly and longitudinally extending wings 48, 50 which give the assembly the appearance of a butterfly. These wings are used to grip the assembly 10 as shown in FIG. 3. They are folded together to provide a finger-gripping surface for insertion of the sharpened end 14 of the needle 12 into a patient. After the needle is in the patient, the wings may be flattened out to their FIG. 1 position and used with tape to secure the assembly 10 on the patient. A couple of strips of tape across the wings 48, 50 will hold the needle 12 in position in a vein. Medication or other material then may be introduced to the patient through the flexible tube 22 which is in communication with the needle 12. Of course, blood may be removed from the patient through the needle 12 and tube 22.

When the needle 12 is in its use position as shown in FIG. 2 and FIG. 3, and since the needle 12 and the sleeve 20 are slidably movable within the tube 30, the wings 48, 50 may preferably be provided with struts 52, 54 respectively which are longitudinally narrow, radially extending stiffeners on the bottoms of the wings. Since these struts 52, 54 are molded integrally with the plastic tube 30 and wings 48, 50, folding the wings upwardly to provide the gripping means will cause the tube 30 to be squeezed inwardly to resist rearward movement of the needle 12 from its FIGS. 2 and 3 position when it is inserted into a patient.

The struts 52, 54 may preferably be joined together to bridge over the outer tube 30 as shown in FIG. 1 such that, when the wings 48, 50 are folded together as suggested in FIG. 3, the struts will apply a longitudinal force toward the centerline of the tube 30 deforming it into an oval shape to grip the needle 12 with a strong gripping action. Preferably, the gripping action may occur on the sleeve 20 on the needle 12 even to the point of indenting the sleeve.

A needle cover tube 60 connected to the forward end of the tube 30 is provided and may be removably connected as indicated at 62 to the forward end 32 of the tube 30. This cover tube 60 may preferably be integrally molded with the tube 30 with a weakened section right at the point 62. It will be appreciated that other techniques may be provided for joining the cover tube 60 to the tube 30. When the integrally molded cover tube is broken away, it will not thereafter stay on the needle. This discourages efforts to replace the cover tube 60.

What is claimed is:

1. A needle assembly comprising an outer tube having a front end and a rear end portion, means providing a constriction at said front end, a rigid, straight, hollow needle having a sharpened front end and a rear end, tube means for providing communication with said needle, said tube means having a front portion connected to said rear end of said needle and a flexible trailing portion, said needle and at least said front portion of said tube means being slidably disposed in said outer tube with said sharpened end extending through said constriction at said front end of said outer tube to penetrate a patient, and said rear end portion of said outer tube with said flexible trailing portion of said tube means reciprocally disposed therein having a curved portion to capture said needle in said outer tube, said outer tube having a length such that, when said trailing portion is pulled rearwardly, said needle moves rearwardly in said outer tube to be totally contained therein with said sharpened end inwardly from said constriction in a protected position.

2. The assembly of claim 1 in which said tube means front portion includes a plastic tube sleeved over and attached to said needle rear end, said plastic tube having a diameter slidably movable in said outer tube and restricted against forward movement by said constriction at said outer tube front end.

3. The assembly of claim 2 in which said plastic tube is restricted against rearward movement by said curved portion.

4. The assembly of claim 2 in which said outer tube is formed of plastic with integrally formed, diametrically opposed flexible plastic wings extending radially outwardly and longitudinally therealong to provide means for gripping said assembly, said wings terminating forwardly of said curved portion, said wings providing means for squeezing said outer tube to hold said needle stationary therein when said wings are folded toward each other.

5. A needle assembly comprising a rigid, straight, hollow needle having a sharpened forward end and rearward end, flexible tube means connected to said rearward end of said needle, and an elongated outer tube slidably receiving said needle and at least a forward portion of said tube means, said outer tube having a straight length sufficient totally to receive said needle therein and a forward end formed to pass the forward end of said needle therethrough and to constrict said flexible tube means against forward movement, and said outer tube having a rearward end portion curved to prevent rearward movement of said needle whereby, when said flexible tube is pulled rearwardly from said outer tube, said needle is pulled rearwardly to a position totally within said outer tube to protect said sharpened end.

6. The assembly of claim 5 in which said needle is pulled to a canted position within said outer tube when said flexible tube is pulled rearwardly, said canted position being obtained by pulling said needle rearward end into said outer tube rearward end portion.

7. The assembly of claim 5 in which said outer tube is formed as an elongated cylindrical tube without internal restrictions for freely slidably receiving said needle and said at least forward portion of said tube means except for said forward end which is constricted to a size sufficient to pass said needle and to restrict said tube means.

8. The needle assembly of claim 7 in which said outer tube is plastic and its rearward end portion is curved at an angle sufficient to prevent rearward movement of said needle after said needle and said at least forward portion of said flexible tube means is inserted into said outer tube and moved forwardly.

9. The needle assembly of claim 8 in which said outer tube is molded to have diametrically opposed, radially outwardly and longitudinally extending wings which, when folded toward each other, provide a gripping means for said assembly, and means for squeezing said outer tube to hold said needle against rearward movement therein when said wings are folded toward each other, said squeezing means being connected to said wings.

* * * * *